United States Patent [19]

Tahara et al.

[11] Patent Number: 4,568,765

[45] Date of Patent: Feb. 4, 1986

[54] ISOPRENYLAMINE DERIVATIVES

[75] Inventors: Yoshiyuki Tahara, Saitama; Yasuhiro Komatsu, Niiza; Hiroyasu Koyama, Ageo; Reiko Kubota, Hasuda; Teruhito Yamaguchi, Tokyo; Toshihiro Takahashi, Ohi, all of Japan

[73] Assignee: Nisshin Flour Milling Co., Ltd., Japan

[21] Appl. No.: 377,577

[22] Filed: May 12, 1982

[30] Foreign Application Priority Data

May 18, 1981 [JP] Japan .................................. 56-76155

[51] Int. Cl.$^4$ ...................... C07C 87/24; C07C 87/48; A61K 31/135

[52] U.S. Cl. ...................................................... 564/509; 564/142; 564/143; 564/152; 564/155; 564/367; 564/368

[58] Field of Search .............................. 564/509, 512

[56] References Cited

U.S. PATENT DOCUMENTS

| 3,641,155 | 2/1972 | Tilford et al. | 564/509 X |
| 3,665,040 | 5/1972 | Ruegg et al. | 564/509 X |
| 3,706,733 | 12/1972 | Henrick et al. | 564/509 X |
| 4,034,040 | 7/1977 | Cronin et al. | 564/509 X |
| 4,340,760 | 7/1982 | Tahara et al. | 564/509 X |

Primary Examiner—Robert V. Hines
Attorney, Agent, or Firm—Abelman, Frayne, Rezac & Schwab

[57] ABSTRACT

This invention relates to new isoprenylamine derivatives and acid addition salts thereof, which are useful as medicines for controlling virus infection of vertebrate animals, or the intermediates therefor.

5 Claims, No Drawings

ISOPRENYLAMINE DERIVATIVES

There are known heretofore various substances, which have been decided to have preventive or alleviative effects on diseases caused by virus whose host is a vertebrate animal, or which have been recognized to be capable of alleviating symptoms of the diseases by significantly enhancing antibody activity in the animal. Antivirotics reported so far include interferon, substances capable of inducing interferon, i.e. inducers (interferon inducers), and synthetic substances, such as amantadine hydrochloride or methisazone, which directly exert inhibitory effect on virus propagation. Interferon is glycoprotein having antiviral and antitumor activities, said glycoprotein being produced in situ by cells of a vertebrate animal when the cells are infected with virus, and has been known to be effective in therapy of infectious viral disease as well as of cancer. Known inducers, which induce interferon in vertebrate animals through a process other than virus infection, include natural high molecular substances such as double strand ribonucleic acid of bacteriophage of a certain species, or synthetic high molecular substances such as double strand ribonucleic acid, typical of which is polyinosinic acid-polycytidylic acid, or low molecular inducers such as tilorone.

In the production of interferon, however, there is involved a problem how to carry out purification thereof, and in fact, no economical process for the production thereof has not been established yet. On the other hand, conventional interferon inducers have not been put to practical use mainly because of toxicity thereof. Synthetic antiviral agents which directly exert inhibitory effect on virus propagation, which are commercially available at present, have a rather narrow range of virus-infected diseases which are curable by administration of said agents, and thus the advent of novel synthetic antiviral agents is earnestly desired. Taking such circumstances into consideration, the present inventors extensively conducted studies in finding compounds capable of producing interferon of high potency and, moreover, having antiviral activity on the biological level, and as the result they have eventually found that compounds represented by the general formula (I) and acid addition salts thereof show excellent interferon-inducing ability and, at the same time, demonstrate excellent antiviral activity even in the biological test.

Thus, the present invention is to provide a new class of an isoprenylamine derivative represented by the following general formula

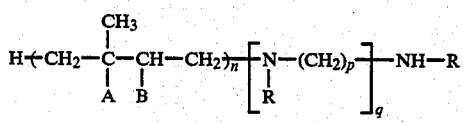

wherein n is 2 to 10, A and B are individually hydrogen atom or A and B jointly form a single bond, and when n is 4, A and B may be a combination of the aforesaid two cases, R is hydrogen, benzoyl, benzyl, lower alkyl or lower acyl, p is 2 or 3, and q is at least 2, particularly 2 or 3, and acid addition salts thereof. For the production of isoprenylamine derivatives represented by the general formula (I) and acid addition salts thereof, there may be adopted the known procedure in which isoprenyl alcohol (e.g. decaprenol, solanesol, phytol or geraniol) represented by the general formula

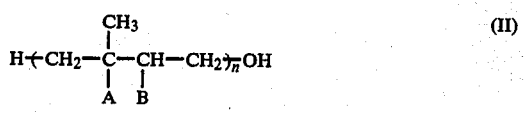

wherein A, B and n are as defined above, is first converted into a corresponding halide (e.g. geranyl bromide, solanesyl bromide, phytyl bromide or decaprenyl bromide) or arylsulfonic acid ester (e.g. decaprenyl tosylate or solanesyl tosylate) and the resulting halide or ester is then allowed to react in the presence or absence of a base with a compound represented by the general formula

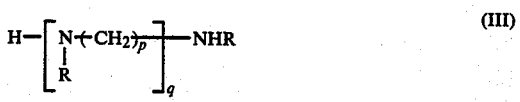

wherein R, p and q are as defined above.

This reaction is usually carried out in an organic solvent. Preferably usable as organic solvents in the reaction are common solvents such as methanol, ethanol, chloroform, isopropyl ether, benzene and ethyl acetate. The reaction is carried out by using a large excess of the amino compound represented by the general formula (III), or carried out at a temperature ranging from room temperature up to 100° C. in the presence of a base (e.g. sodium or potassium hydroxide or sodium or potassium carbonate). After the completion of the reaction, a desired isoprenylamine derivative can be produced by treating the resultant reaction liquid according to usual isolation and purification procedures such as extraction, concentration, column chromatography or crystallization. For the production of compounds of the general formula (I), in which R is benzoyl, benzyl, lower alkyl or lower acyl, there may be adopted another process in which a compound represented by the general formula (IV)

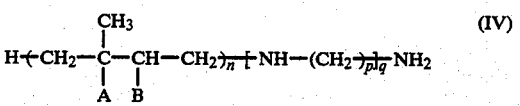

wherein A, B, n, p and q are as defined above, is obtained under the same reaction conditions as above, and the resulting compound is then allowed to react in the presence of a base (e.g. such tertiary amine as pyridine or triethylamine) at a temperature of 0° to 50° C. with a compound represented by the general formula

wherein R' is methyl or phenyl and X is halogen atom, to obtain a compound represented by the general formula (VI)

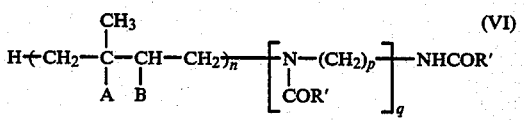

wherein R' represents methyl or phenyl, and A, B, n, and q are as defined above, and the resulting compound is charged with a reducing agent (e.g. lithium aluminum hydride) and allowed to undergo reaction in an organic solvent. Preferably usable as solvents in the reaction are ether, tetrahydrofuran and the like. The reaction is preferably carried out at a temperature ranging from room temperature up to 60° C. After the completion of the reaction, a desired isoprenylamine derivative can be produced by treating the resultant reaction liquid according to usual isolation and purification procedures such as extraction, concentration, column chromatography, crystallization and the like.

An acid addition salt of the isoprenylamine derivative thus produced can be obtained by mixing said derivative in an appropriate solvent (e.g. acetone or ethyl acetate) with a desired acid to form a salt and applying such means as concentration or crystallization to the salt. The acid addition salts suitable for use as medicines include, for example, those with hydrochloric acid, acetic acid, citric acid, fumaric acid, lactic acid and the like.

Illustrated below are preparative examples of isoprenylamine derivatives of the present invention.

PREPARATIVE EXAMPLE 1

N-decaprenyltriethylenetetramine

To a chloroform solution (100 ml) containing triethylenetetramine (47.0 g) was added dropwise at room temperature a chloroform solution (100 ml) containing decaprenyl bromide (40 g) over a period of 1 hour with stirring, and the mixture was further stirred at room temperature for 3 hours. The reaction liquid was concentrated under reduced pressure, and the concentrate was extracted with ethyl acetate. The extract was washed with water and saturated saline, dried over anhydrous sodium sulfate and then concentrated under reduced pressure to obtain a concentrate (41.4 g). To a solution of the thus obtained concentrate in isopropyl ether (100 ml) was added sodium carbonate (20 g). To the mixture while cooling with ice-water was added dropwise trifluoroacetic anhydride (30 ml) over a period of 1 hour with stirring, and the mixture was further stirred for 3 hours while cooling with ice-water. The reaction liquid is filtered to separate insolubles therefrom, and the filtrate was concentrated under reduced pressure. The concentrate was charged with benzene (about 50 ml) and further concentrated under reduced pressure. The concentrate (43.9 g) was chromatographed with a benzene-ethyl acetate mixture over a column packed with silica gel (450 g) to obtain N-decaprenyl-N,N', N'', N'''-tetratrifluoroacetyltriethylenetetramine (10.1 g). A mixture of the thus obtained N-decaprenyl-N,N',N'',-N'''-tetratrifluoroacetyltriethylenetetramine (10.1 g) and an ethanol solution (100 ml) of 10% potassium hydroxide was heated under reflux for 1 hour. The reaction liquid was charged with water (300 ml), and the mixture was extracted with ethyl acetate. The extract was washed with water and saturated saline, dried over anhydrous sodium sulfate and then concentrated under reduced pressure to obtain as an oily product N-decaprenyltriethylenetetramine (9.5 g) represented by the following formula

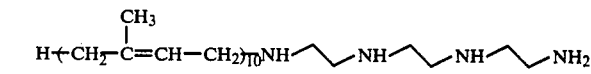

Given below are measured values of physical properties of the title compound.

| $n_D^{28.0} = 1.5109$ | |
|---|---|
| N.M.R. (δvalue in CDCl$_3$): | |
| 4.9–5.3 | (10H, br) |
| 3.20 | (2H, d, J = 7Hz) |
| 2.72 | (12H, s) |
| 2.00 | (36H, br) |
| 1.60 | (33H, s) |

| Elementary analysis (as D$_{56}$H$_{98}$N$_4$ 2H$_2$O): | | |
|---|---|---|
| | Calcd. | Found |
| C (%) | 77.90 | 77.98 |
| H (%) | 11.91 | 11.75 |
| N (%) | 6.49 | 6.36 |

PREPARATIVE EXAMPLE 2

N-decaprenyl-N,N',N'',N'''-tetrabenzyltriethylenetetramine tetrahydrochloride

To a chloroform solution (50 ml) containing N-decaprenyltriethylenetetramine (5.0 g) obtained in Preparative Example 1 was added pyridine (10 ml), and thereto was added dropwise with stirring a chloroform solution (30 ml) containing benzoyl chloride (4.5 g) over a period of 1 hour while cooling on an ice bath, and the resulting mixture was further stirred at room temperature for 2 hours. The reaction liquid was extracted with isopropyl ether, and the extract was washed with water, 5% hydrochloric acid, 5% aqueous sodium hydrogen carbonate solution and saturated saline in that order and dried over anhydrous sodium sulfate, and then concentrated under reduced pressure. The concentrate (6.7 g) was treated by chromatography with a chloroform-ethyl acetate mixture over a column packed with silica gel (100 g) to obtain N-decaprenyl-N,N',N'',N'''-tetrabenzoyltriethylenetetramine (4.2 g). To an anhydrous diethyl ether solution (50 ml) of the thus obtained N-decaprenyl-N,N',N'',N'''-tetrabenzoyltriethylenetetramine (4.2 g) was added in small portions at room temperature lithium alminum hydride (2.0 g). After the completion of the dropwise addition, the mixture was stirred at room temperature for 1 hour and then heated under reflux for 3 hours with stirring. The reaction liquid was charged with a 10% aqueous sodium hydroxide solution (100 ml) and then extracted with isopropyl ether. The extract was washed with water and saturated saline, dried over anhydrous sodium sulfate and then concentrated under reduced pressure. The concentrate (3.8 g) was dissolved in acetone (100 ml), charged with a hydrogen chloride-ether solution to weakly acidic and then concentrated under reduced pressure to dryness to obtain N-decaprenyl-N,N',N'',N'''-tetrabenzyltriethylenetetramine tetrahydrochloride (3.8 g) represented by the following formula.

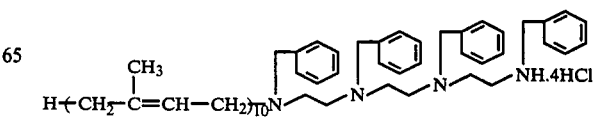

Given below are measured values of physical properties of the title compound.

| Melting point: Caramel-like state N.M.R. (δvalue in CDCl₃) (Free base): | |
|---|---|
| 7.13 | (20H, s) |
| 4.9–5.3 | (10H, br) |
| 3.46 | (2H, s) |
| 3.40 | (6H, br-s) |
| 2.90 | (2H, d, J = 7Hz) |
| 2.2–2.6 | (12H, m) |
| 2.00 | (36H, br) |
| 1.60 | (33H, s) |

| Elementary analysis as ($C_{84}H_{122}N_4\cdot 4HCl\cdot 3/2H_2O$): | | |
|---|---|---|
| | Calcd. | Found |
| C (%) | 74.14 | 74.32 |
| H (%) | 9.55 | 9.65 |
| N (%) | 4.12 | 4.11 |

PREPARATIVE EXAMPLE 3

N-geranyl-N,N',N'',N'''-tetraethyltriethylenetetramine

To a chloroform solution (200 ml) containing triethylenetetramine (60 g) was added dropwise with stirring a chloroform solution (100 ml) containing geranyl bromide (20 g) at room temperature, and the mixture was further stirred at room temperature for 3 hours. After the completion of the reaction, the reaction liquid was concentrated under reduced pressure to remove the chloroform therefrom, and the concentrate was extracted with ethyl acetate. The extract was washed with a 10% aqueous sodium hydroxide solution and saturated saline, dried over anhydrous sodium sulfate and then concentrated under reduced pressure to obtain a concentrate (21 g). The concentrate was dissolved in benzene (100 ml), charged with acetic anhydride (30 ml) and sodium acetate (10 g) and then heated under reflux for 4 hours with stirring. The reaction liquid poured in a 10% aqueous sodium hydroxide solution (300 ml) and then extracted with ethyl acetate. The extract was washed with saturated saline, dried over anhydrous sodium sulfate and then concentrated under reduced pressure. The concentrate (23.5 g) was treated by chromatography with an ethanol-ethyl acetate mixture over a column packed with alumina (250 g) to obtain an oily N-geranyl-N,N',N'',N'''-tetraacetyltriethylenetetramine (9.3 g). The thus obtained N-geranyl-N,N',N'',N'''-tetraacetyltriethylenetetramine (9.3 g) was dissolved in anhydrous tetrahydrofuran (100 ml), and thereto was added in small portions lithium aluminum hydride at room temperature with stirring. The mixture was stirred at room temperature for 1 hour and then heated under reflux with stirring for 3 hours. After cooling, the reaction liquid was charged with a 20% aqueous sodium hydroxide solution (5 ml), filtered to separate insolubles therefrom and then the filtrate was concentrated under reduced pressure. The concentrate was extracted with isopropyl ether, washed with water and saturated saline, dried over anhydrous sodium sulfate and the concentrated under reduced pressure to obtain as an oily product N-geranyl-N,N',N'',N'''-tetraethyltriethylenetetramine (5.1 g) represented by the following formula.

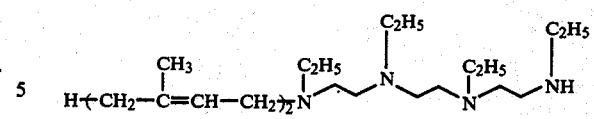

Given below are measured values of physical properties of the title compound.

| $n_D^{22}$ = 1.4851 N.M.R. (δvalue in CDCl₃): | |
|---|---|
| 5.0–5.4 | (2H, m) |
| 3.10 | (2H, d, J = 7Hz) |
| 0.8–2.9 | (48H, m) |

| Elementary analysis (as $C_{24}H_{50}N_4\cdot H_2O$): | | |
|---|---|---|
| | Calcd. | Found |
| C (%) | 69.85 | 69.98 |
| H (%) | 12.70 | 12.81 |
| N (%) | 13.58 | 13.35 |

PREPARATIVE EXAMPLE 4

N-phytyl-N,N',N'',N'''-tetraethyltriethylenetetramine

To a chloroform solution (200 ml) containing triethylenetetramine (60 g) was added dropwise with stirring at room temperature a chloroform solution (100 ml) containing phytyl bromide (31 g) over a period of 1 hour, and the mixture was further stirred at room temperature for 3 hours. After the completion of the dropwise addition, the reaction liquid was concentrated under reduced pressure to remove the chloroform therefrom, and the concentrate was extracted with ethyl acetate. The extract was washed with a 10% aqueous sodium hydroxide solution and saturated saline, dried over anhydrous sodium sulfate and then concentrated under reduced pressure to obtain a concentrate (30 g). The concentrate was dissolved in benzene (100 ml), charged with acetic anhydride (30 ml) and sodium acetate (10 g), and the resulting mixture was heated under reflux for 4 hours with stirring. After the completion of the reaction, the reaction liquid was poured in a 10% aqueous sodium hydroxide solution (300 ml) and then extracted with ethyl acetate. The extract was washed with saturated saline, dried over anhydrous sodium sulfate and then concentrated under reduced pressure. The concentrate (41 g) was treated by chromatography with an ethanol-ethyl acetate mixture over a column packed with alumina (250 g) to obtain an oily N-phytyl-N,N',N'',N'''-tetraacetyltriethylenetetramine (11 g). The thus obtained N-phytyl-N,N',N'',N'''-tetraacetyltriethylenetetramine (11 g) was dissolved in anhydrous tetrahydrofuran (100 ml), and thereto was added in small portions lithium aluminum hydride at room temperature with stirring. The mixture was stirred at room temperature for 1 hour and then heated under reflux with stirring for 3 hours. After cooling, the reaction liquid was charged with a 20% aqueous sodium hydroxide solution (5 ml), filtered to separate insolubles therefrom and then the filtrate was concentrated under reduced pressure. The concentrate was extracted with isopropyl ether, washed with water and saturated saline, dried over anhydrous sodium sulfate and then concentrated under reduced pressure to obtain as an oily product N-phytyl-N,N',N'',N'''-tetraethyltriethylenetetramine (7.3 g) represented by the following formula.

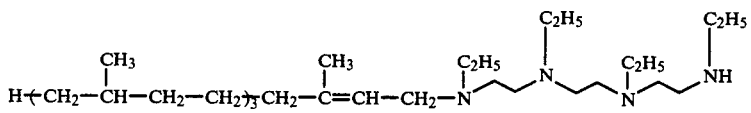

Given below are measured values of physical properties of the title compound.

$n_D^{22} = 1.4721$

N.M.R. (δ value in CDCl₃):

| 5.30 | (1H, t, J = 7Hz) |
| 3.05 | (2H, d, J = 7Hz) |
| 2.0–2.9 | (20H, m) |
| 0.8–2.0 | (49H, m) |

Elementary analysis (as $C_{34}H_{72}N_4 \cdot H_2O$):

| | Calcd. | Found |
|---|---|---|
| C (%) | 73.58 | 73.78 |
| H (%) | 13.44 | 13.51 |
| N (%) | 10.10 | 7.89 |

PREPARATIVE EXAMPLE 5

N-decaprenyldiethylenetriamine

The same procedures as in Preparative Example 1 were carried out for the reaction of decaprenyl bromide with diethylenetriamine thereby to obtain N-decaprenyldiethylenetriamine represented by the following formula, the measured values of physical properties of which were as shown in Table 1.

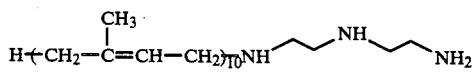

PREPARATIVE EXAMPLE 6

N-solanesyltriethylenetetramine tetrahydrochloride

The same procedures as in Preparative Example 1 were carried out for the reaction of solanesyl bromide with triethylenetetramine thereby to obtain N-solanesyltriethylenetetramine tetrahydrochloride represented by the following formula, the measured values of physical properties of which were as shown in Table 1.

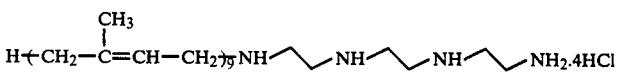

PREPARATIVE EXAMPLE 7

N-decaprenyldipropylenetriamine trihydrochloride

The same procedures as in Preparative Example 1 were carried out for the reaction of decaprenyl bromide with dipropylenetriamine to obtain N-decaprenyldipropylenetriamine trihydrochloride represented by the following formula, the measured values of physical properties of which were as shown in Table 1.

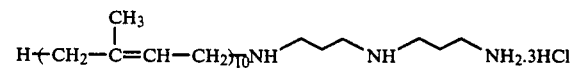

In tables that follow, "D" represents decaprenyl, "S" represents solanesyl and "Phy" represents phytyl in each chemical structural formula as indicated.

TABLE 1

| Structural formula | Molecular formula | $n_D$ or m.p. | N.M.R. (δ value in CDCl₃) | Calcd. (%) C | H | N | Found (%) C | H | N |
|---|---|---|---|---|---|---|---|---|---|
| D—NH⁀NH⁀NH⁀NH₂ | $C_{54}H_{93}N_3 \cdot H_2O$ | $n_D^{27.5} = 1.5177$ | 4.9–5.3(10H,br) 3.20(2H,d,J = 7Hz) 2.71(8H,s) 2.00(36H, br) 1.60(33H,s) (Free) | 80.84 | 11.93 | 5.24 | 80.93 | 11.84 | 5.12 |
| S—NH⁀NH⁀NH⁀NH₂·4HCl | $C_{51}H_{90}N_4 \cdot 4HCl \cdot 3/2H_2O$ | Caramel-like | 4.9–5.3(9H,br) 3.20(2H,d,J = 7Hz) 2.72(12H,s) 2.00(32H) 1.60(30H) (Free) | 65.71 | 10.49 | 6.01 | 65.94 | 10.54 | 5.91 |
| D—NH⁀NH⁀NH₂·3HCl | $C_{56}H_{97}N_3 \cdot 3HCl \cdot 2H_2O$ | Caramel-like | 4.9–5.3(10H,br) 3.20(2H,d,J = 7Hz) 2.50–2.9(8H,m) 2.00(36H,br) 1.60(37H,s) (Free) | 70.22 | 10.94 | 4.39 | 70.15 | 10.71 | 4.28 |

Physiological effects of the isoprenylamine derivatives of the present invention are illustrated below in detail.

(1) Effect on Mice Infected with Vaccinia Virus

Groups, each consisting of 10 ICR female mice weighing about 15 g, were intravenously injected a dilute solution (0.1 ml) of vaccinia virus at a portion 2 cm from the base of a tail. On the 8th day after the inoculation, the number of lesions in the form of small pocks on the tail surface was counted after dyeing the tail with an ethanol solution of 1% fluorescein and 0.5% methylene blue. Each test compound suspended in a surfactant solution was administered intraperitoneally at a rate of 50 mg/kg to the mice 24 hours before inoculation of the virus, whereby antivirus activity of the test compound was evaluated in terms of inhibition of tail lesions as calculated in each test group against a group to which only the surfactant solution had been administered. The rate of tail lesion inhibition of each test compound is shown in Table 2.

TABLE 2

| Test compound (Structural formula) | Prevention from vaccinia infection (Pock inhibition rate %) |
|---|---|
| D—NH—/\/—NH—\/\—NH—/\/—NH$_2$ | 87.9 |
| D—NH—/\/—NH—\/\—NH$_2$ | 51.9 |
| S—NH—/\/—NH—\/\—NH—/\/—NH$_2$.4HCl | 76.1 |

(2) Anti-Tumor Activity

Groups, each consisting of 6 Balb/c male mice weighing about 20 g, were intraperitoneally administered $5 \times 10^5$ of tumor cells KN$_7$-8. Each test compound suspended in a surfactant solution was intraperitoneally administered (each time at a rate of 30 mg/kg) to the mice 24 hours before inoculation of the tumor cells and on the second day and the fifth day after the inoculation, totalling 3 times, and the anti-tumor activity was evaluated in terms of number of survivors on the 30th day after the inoculation. The number of survivors relative to each test compound is shown in Table 3.

TABLE 3

| Test compound (Structural formula) | Anti-tumor activity (Survivor on the 30th day) |
|---|---|
| D—NH—/\/—NH—\/\—NH—/\/—NH$_2$ | 5/6 |
| D—NH—/\/—NH—\/\—NH$_2$ | 1/6 |
| S—NH—/\/—NH—\/\—NH—/\/—NH$_2$ 4HCl | 3/6 |
| D—NH—/\/—NH$_2$.3HCl | 2/6 |

(3) Human Interferon Inducing Activity (in vitro)

Interferon was induced according to the method of Edward A. Havell et al. by treating normal diploid cells (fibroblast) originated from human being with each test compound (in the form of ethanol solution diluted with PBS (−), 25 n molar suspension). Using the radioisotope microassay method of H. Ishitsuka et al., interferon was measured in terms of 3H-uridine-uptake inhibition rate. The rate of 3H-uridine-uptake inhibition of each test compound as measured is shown in Table 4.

TABLE 4

| Test compound (Structural formula) | Human interferon (in vitro) 3H—uridine-uptake inhibition rate % |
|---|---|
| D—N(CH$_2$Ph)—/\—N(CH$_2$Ph)—\/—N(CH$_2$Ph)—/\—NH(CH$_2$Ph).4HCl | 23.2 |
| D—NH—/\/—NH—\/\—NH$_2$ | 15.1 |

(4) Anti-vaccinia virus activity (in vitro)

Virus plaque-formation inhibition rate of a test compound was obtained by treating vero cells originated from the kidney of African green monkey with the test compound suspension (the compound in the form of ethanol solution was suspended in Hanks culture liquid, 50 n molar concentration) and the virus diluted solution. The inhibition rate of the test compound as measured is shown in Table 5.

TABLE 5

| Test compound (Structural formula) | Anti-vaccinia virus activity (in vitro) (Plaque inhibition rate %) |
|---|---|
| D—NH—/\/—NH—\/\—NH—/\/—NH$_2$ | 44.5 |

(5) Toxicity

Using ddY male mice weighing 20–25 g, 50% lethal dose of each test compound when intravenously administered was obtained, the results of which are shown in Table 6.

TABLE 6

| Test compound | LD$_{50}$ (mg/kg) |
|---|---|
| Phy—N(C$_2$H$_5$)—/\—N(C$_2$H$_5$)—\/—N(C$_2$H$_5$)—/\—NH(C$_2$H$_5$) | 34 |
| D—NH—\—NH—\—NH—\—NH$_2$ | 57 |
| D—NH—\—NH—\—NH—\—NH$_2$.4HCl | 21 |

As is clear from the foregoing test results, the active ingredients of the present invention have interferon-inducing activity in vivo and, at the same time, are low in toxicity while showing excellent antiviral activity. In the light of the fact that the strict correlation of interferon activity with the individual antivirus activities is not always observed for the present ingredients, there is considered also a possibility that the antivirus activities of said ingredients at biological leval are concerned not only in interferon but also in other defensive mechanism of host. As diseases of human being caused by virus, there are known a number of symptoms, for example, herpes-infected diseases such as herpes simplex, influenza, measles, etc. Accordingly, when the active ingredients of the present invention are used for prevention from virus infection and for the treatment of virus-infected diseases, they are administered to patients by such technique involving oral, inhalant, or the like administration as well as subcutaneous, intramuscular and intravenous injection. According to the condition of patient such as age, symptom and route by which the ingredient is administered, the active ingredient of the present invention is used a dose of 0.5–20 mg/kg, preferably 3–5 mg/kg several times (2–4 times) per day.

The active ingredients of the present invention can be formulated into compositions for medication, for example, tablets, capsules, granules, powder, liquid preparation for oral use, eye lotions, suppositiories, ointments, injections and the like.

When the present active ingredients are orally administered, they may be formulated into tablets, capsules, granules or powder. These solid preparations for oral use may contain commonly used excipients, for example, silicic anhydride, metasilicic acid, magnesium alginate, synthetic aluminum silicate, lactose, cane sugar, corn starch, microcrystalline cellulose, hydroxypropylated starch or glycine and the like; and binders, for example, gum arabic, gelatin, tragacanth, hydroxypropyl cellulose, or polyvinyl pyrrolidone; lubricants, for example, magnesium stearate, talc or silica; disintegrating agents, for example, potato starch and carboxymethyl cellulose calcium; or wetting agents, for example, polyethylene glycol, sorbitan monooleate, polyoxyethylene hydrogenated castor oil, sodium laurylsulfate and the like. In preparing soft capsules, in particular, the present active ingredients may be formulated by dissolving or suspending them in polyethyleneglycol or commonly used oily substrates such as sesame oil, peanut oil, germ oil, fractionated coconut oil such as Miglyol ®, or the like. Tablet or granule preparations may be coated according to the usual method.

Liquid preparation for oral use may be in the form of aqueous or oily emulsion or syrup, or alternatively in the form of dry product which can be re-dissolved before use by means of a suitable vehicle. To these liquid preparations, there may be added commonly used additives, for example, emulsifying aids such as sorbitol syrup, methyl cellulose, gelatin, hydroxyethyl cellulose and the like; or emulsifiers, for example, lecithin, sorbitan monooleate, polyoxyethylene hydrogenated castor oil, non-aqueous vehicles, for example, fractionated coconut oil, almond oil, peanut oil and the like; or antiseptics, for example, methyl p-hydroxybenzoate, propyl p-hydroxybenzoate, or sorbic acid. Further, these preparations for oral use may contain, if necessary, preservatives, stabilizers and the like additives.

In case where the present active ingredients are administered in the form of non-oral suppository, they may be formulated according to the ordinary method using oleophilic substrates such as cacao oil or Witepsol ®, or may be used in the form of rectum capsule obtained by wrapping a mixture of polyethylene glycol, sesame oil, peanut oil, germ oil, fractionated coconut oil and the like in a gelatin sheet. The rectum capsule may be coated, if necessary, with waxy materials.

When the present active ingredients are used in the form of injection, they may be formulated into preparations of oil solution, emulsified solution or aqueous solution, and they may contain commonly used emulsifiers, stabilizers or the like additives.

According to the method of administration, the above-mentioned compositions can contain the present active ingredients in an amount of at least 1%, preferably 5 to 50%.

The procedure of formulating the present active ingredients into various preparations is illustrated below with reference to pharmaceutical examples.

PHARMACEUTICAL EXAMPLE 1

Hard Capsule Preparations for Oral Use

A mixture of 25 g of N-decaprenyltriethylenetetramine and 7.5 g of polyoxyethylene castor oil in acetone was mixed with 25 g of silicic anhydride. After evaporation of the acetone, the mixture was mixed further with 5 g of calcium carboxymethylcellulose, 5 g of corn starch, 7.5 g of hydroxypropylcellulose and 20 g of microcrystalline cellulose, and 30 ml of water was added thereto and kneaded to give a granular mass. The mass was pelletized by means of a pelletizer (ECK pelletizer of Fuji Paudal Co., Japan) equipped with No. 24 mesh (B.S.) screen to obtain granules. The granules were dried to less than 5% moisture content and screened with No. 16 mesh (B.S.) screen. The screened granules were capsuled by means of a capsule filling machine so as to be contained in an amount of 190 mg per capsule.

PHARMACEUTICAL EXAMPLE 2

Soft Capsule Preparation for Oral Use

A homogeneous solution was prepared by mixing 50 g of N-decaprenyl-N,N',N'',N'''-tetrabenzyltriethylenetetramine tetrahydrochloride with 130 g of polyethylene glycol (Macrogol 400 g). Separately, a gelatin solution was prepared which contained 93 g of gelatin, 19 g of glycerin, 10 g of D-sorbitol, 0.4 g of ethyl p-hydroxybenzoate, 0.2 g of propyl p-hydroxybenzoate and 0.4 g of titanium oxide and which was used as a capsule film-forming agent. The previously obtained solution, together with the capsule film forming agent, was treated with a manual type flat punching machine to obtain soft capsules each having the contents of 180 mg.

PHARMACEUTICAL EXAMPLE 3

Injections

A mixture of 5 g of N-geranyl-N,N',N'',N'''-tetraethyltriethylenetetramine, an appropriate amount of peanut oil and 1 g of benzyl alcohol was made a total volume of 100 cc by addition of peanut oil. The solution was portionwise poured in an amount of 1 cc under asepsis operation into an ampule which was then sealed.

PHARMACEUTICAL EXAMPLE 4

Injections

A mixture of 1.0 g of N-decaprenyltriethylenetetramine, 5.0 g of Nikkol HCO 60 (a trade-name) (hydrogenated castor oil polyoxyethylene-60 mols-ether), 20 g of propylene glycol, 10 g of glycerol and 5.0 g of ethyl alcohol was mixed with 100 ml of distilled water and stirred. Under asepsis operation, the solution was portionwise poured in an amount of 1.4 ml into an ampule which was then sealed.

What we claim is:

1. An isoprenylamine derivative represented by the general formula

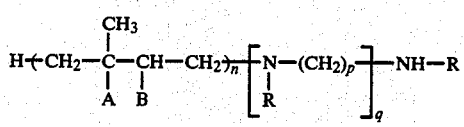

wherein n is 9 or 10, wherein when n is 9 or 10, A and B jointly form a single bond, forming a solanesyl and decaprenyl group, respectively, R is hydrogen or lower alkyl, p and q are each 2 or 3, and the acid addition salts thereof.

2. The compound as claimed in claim 1, which is N-decaprenyl-triethylenetetramine.

3. The compound as claimed in claim 1, which is N-decaprenyl-diethylenetriamine.

4. The compound as claimed in claim 1, which is N-solanesyl-triethylenetetramine quadhydrochloride.

5. The compound as claimed in claim 1, which is N-decaprenyl-dipropylenetriamine trihydrochloride.

* * * * *